United States Patent [19]

Madden

[11] Patent Number: 4,963,297

[45] Date of Patent: Oct. 16, 1990

[54] SPONTANEOUS VESTICULATION OF MULTILAMELLAR LIPOSOMES

[75] Inventor: Thomas D. Madden, Vancouver, Canada

[73] Assignee: The Liposome Company, Inc., Princeton, N.J.

[21] Appl. No.: 136,267

[22] Filed: Dec. 22, 1987

[51] Int. Cl.$^5$ .................... A61K 9/133; B01J 13/02
[52] U.S. Cl. ..................... 264/4.3; 264/4.1; 424/450; 428/402.2; 436/829
[58] Field of Search ............... 264/4.1, 4.3; 424/450; 436/829

[56] References Cited

U.S. PATENT DOCUMENTS

| | | | |
|---|---|---|---|
| 3,993,754 | 11/1976 | Rahman et al. | 424/450 X |
| 4,145,410 | 3/1979 | Sears | 424/450 |
| 4,224,179 | 9/1980 | Schneider | 264/4.6 |
| 4,235,871 | 11/1980 | Papahadjopoulos et al. | 424/450 |
| 4,310,505 | 1/1982 | Baldeschwieler et al. | 424/1.1 |
| 4,515,736 | 5/1985 | Deamer | 264/4.3 |
| 4,522,803 | 6/1985 | Lenk et al. | 424/1.1 |
| 4,588,578 | 5/1986 | Fountain et al. | 424/1.1 |
| 4,619,794 | 10/1986 | Hauser | 264/4.1 |
| 4,673,567 | 6/1987 | Jizomoto | 264/4.3 X |
| 4,762,720 | 8/1988 | Jizomoto | 424/450 |

FOREIGN PATENT DOCUMENTS

WO86/01103 2/1986 PCT Int'l Appl. .
WO87/00043 1/1987 PCT Int'l Appl. .

OTHER PUBLICATIONS

Bangham, et al., Diffusion of Univalent Ions across the Lamellas of Swollen Phospholipids, 1965, J. Biol. Chem., 12:238-252.
Cullis and de Kruiff, Lipid Polymorphism and the Functional Roles of Lipids in Biological Membranes, 1979, Biochim, Biophys, Acta., 559:339.
Cullis et al., Structural Properties and Functional Roles of Phospholipids in Biological Membranes, 1985, in Phospholipids and Cellular Regulation, J. F. Kuo, ed., CRC Press, Boca Raton, FL.
Vail, et al., Phase Changes of Cardiolipin Vesicles Mediated by Divalent Cations, 1979, Biochim, Biophys. Acta., 551:74.
Hope et al., Generation of Multilamellar and Unilamellar Phospholipid Vesicles, 1986, Chem. Phys. Lipids, 40:89.
Wilschut et al., Studies on the Mechanism of Membrane Fusion; Kinetics of Calcium Ion Induced Fusion of Phophatidylserine Vesicles Followed by a New Assay for Mixing of Aqueous Vesicle Contents, 1980, Biochemistry, 19:6011.
Poznansky, et al., Biological Approaches to the Controlled Delivery of Drugs: A Critical Review, 1984, Pharmacol. Rev., 36:227.
Gruner, et al., Novel Multilayered Lipid Vesicles: Comparison of Physical Characteristics of Multilamellar Liposomes and Stable Plurilamellar Vesicles, 1985, Biochemistry, 24:2833.
Mayer, et al., Vesicles of Variable Sizes Produced by a Rapid Extrusion Procedure, 1986, Biochim, Biophys. Acta., 858:161.
Huang, Studies on Phosphatidylcholine Vesicles, Formation and Physical Characteristics, 1969, Biochemistry, 8:344.
Hope et al., Production of Large Unilamellar Vesicles by a Rapid Extrusion Procedure, Characterization of (List continued on next page.)

Primary Examiner—Richard D. Lovering
Attorney, Agent, or Firm—Bloom, Allen; Catherine L. Kurtz

[57] ABSTRACT

A new method is disclosed for making unilamellar vesicles from multilamellar vesicles. Such vesicles are formed without the use of physical of chemical disruption processes known in the art for forming unilamellar vesicles. The liposomes are incubated at neutral pH at or near the transition temperature of the lipids used, in low ionic strength media such as distilled water. The liposomes may comprise bioactive agents and may be used in vivo or in vitro.

10 Claims, 3 Drawing Sheets

OTHER PUBLICATIONS

Size Distribution Trapped Volume and Ability to Maintain a Membrane Potential, 1985, Biochim. Biophys. Acta., 812:55.

Hauser, et al., Spontaneous Vesiculation of Phospholipids: A Simple and Quick Method of Forming Unilamellar Vesicles, 1986, Biochemistry, 25:2126.

Gabriel et al., Spontaneous Formation of Stable Unilamellar Vesicles, 1984, Biochemistry, 23:4011.

Hauser, et al., Spontaneous Vesiculation of Aqueous Lipid Dispersions, 1982, Proc. Natl. Acad. Sci., 79:1683.

Gains, Characterisation of Small Unilamellar Vesicles Produced in Unsonicated Phosphatidic Acid and Phosphatidylcholine-Phosphatidic Acid Dispersions by hP Adjustment, 1983, Biochim. Biophys. Acta., 731:31.

Li, et al., Uniform Preparations of Large Unilamellar Vesicles Containing Anionic Lipids, 1986, Biochemistry, 25:7477.

SPONTANEOUS VESTICULATION OF MULTILAMELLAR LIPOSOMES

BACKGROUND OF THE INVENTION

The present invention is directed to a method of forming unilamellar vesicles without the use of homogenization, filtration, sonication, or extrusion techniques, or other techniques that require energy input to the system, or exposure of lipids to harsh environments. Such environments include for example detergent or extreme pH environments.

Liposomes (vesicles) are completely closed lipid bilayer membranes containing an entrapped aqueous volume. Liposomes may be unilamellar vesicles (possessing a single membrane bilayer) or multilameller vesicles (onion-like structures characterized by multiple membrane bilayers, each separated from the next by an aqueous layer). The bilayer is composed of two lipid monolayers having a hydrophobic "tail" region and a hydrophilic "head" region. The structure of the membrane bilayer is such that the hydrophobic (nonpolar) "tails" of the lipid monolayers orient towards the center of the bilayer while the hydrophilic "heads" orient towards the aqueous phase.

The original liposome preparation of Bangham et al. (J. Mol. Biol., 1965, 12:238-252 involves suspending phospholipids in an organic solvent which is then evaporated to dryness leaving a phospholipid film on the reaction vessel. Next, an appropriate amount of aqueous phase is added, the mixture is allowed to "swell," and the resulting liposomes which consist of multilamellar vesicles (MLVs) are dispersed by mechanical means. MLVs so formed may be used in the practice of the present invention.

Another class of multilamellar liposomes that may be used as the starting liposomes of this invention are those characterized as having substantially equal lamellar solute distribution. This class of liposomes is denominated as stable plurilamellar vesicles (SPLV) as defined in U.S. Pat. No. 4,522,803 to Lenk, et al., reverse phase evaporation vesicles (REV) as described in U.S. Pat. No. 4,235,871 to Papahadjopoulos et al., monophasic vesicles as described in U.S. Pat. No. 4,558,579 to Fountain, et al., and frozen and thawed multilamellar vesicles (FATMLV) wherein the vesicles are exposed to at least one freeze and thaw cycle; this procedure is described in Bally et al., PCT Publication No. 87/00043, Jan. 15, 1987, entitled "Multilamellar Liposomes Having Improved Trapping Efficiencies"; these references are incorporated herein by reference.

Liposomes are comprised of lipids; the term lipid as used herein shall mean any suitable material resulting in a bilayer such that a hydrophobic portion of the lipid material orients toward the interior of the bilayer while a hydrophilic portion orients toward the aqueous phase. The lipids which can be used in the liposome formulations of the present invention are the phospholipids such as phosphatidylcholine (PC) and phosphatidylglycerol (PG), more particularly dimyristoylphosphatidylcholine (DMPC) and dimyristoylphosphatidylglycerol (DMPG). Liposomes may be formed and vesiculated using DMPG, or DMPG mixed with DMPC in, for example, a 3:7 mole ratio, respectively.

During preparation of the liposomes, organic solvents may be used to suspend the lipids. Suitable organic solvents are those with intermediate polarities and dielectric properties, which solubilize the lipids, and include but are not limited to halogenated, aliphatic, cycloaliphatic, or aromatic-aliphatic hydrocarbons, such as benzene, chloroform, methylene chloride, or alcohols, such as methanol, ethanol, and solvent mixtures such as benzene:methanol (70:30). As a result, solutions (mixtures in which the lipids and other components are uniformly distributed throughout) containing the lipids are formed. Solvents are generally chosen on the basis of their biocompatability, low toxicity, and solubilization abilities.

The starting multilamellar liposomes and resulting unilamellar liposomes of the present invention may contain lipid soluble bioactive agents. Such agents are typically associated with the lipid bilayers of the liposomes. As used in the present invention, the term bioactive agent is understood to include any compound having biological activity; e.g., lipid soluble drugs such as non steroidal antinflammatory drugs such as ibuprofen, indomethacin, sulindac, piroxicam, and naproxen, antinoeplastic drugs such as doxorubicin, vincristine, vinblastine, methotrexate and the like, and other therapeutic agents such as anesthetics such as dibucaine, cholinergic agents such as pilocarpine, antihistimines such as benedryl, analgesics such as codeine, anticholinergic agents such as atropine, antidepressants such as imiprimine, antiarrythmic agents such as propranolol, and other lipophilic agents such as dyes, therapeutic proteins and peptides such as immunomodulators, radioopaque agents, fluorescent agents, and the like. Additionally, the vesicles made by the process of this invention may contain bilayer-associated markers or molecules such as proteins or peptides.

The liposomes of the invention may be used in a liposome-drug delivery system. In a liposome-drug delivery system, a bioactive agent such as a drug is associated with the liposomes and then administered to the patient to be treated. For example, see Rahman et al., U.S. Pat. No. 3,993,754; Sears, U.S. Pat. No. 4,145,410; Papahadjopoulos et al., U.S. Pat. No. 4,235,871; Schnieder, U.S. Pat. No. 4,224,179; Lenk et al., U.S. Pat. No. 4,522,803; and Fountain et al., U.S. Pat. No. 4,588,578.

The ability of liposomes to buffer the toxicity of entrapped drugs with little or no decrease in efficacy is becoming increasingly well established. Therefore, there is an increasing need to be able to form liposomes of all types which have these qualities. Unilamellar vesicles are clearly preferred for certain types of in vivo drug delivery over multilamellar vesicles, as well as for studies of membrane-mediated processes. As used as in vivo delivery vehicles, for example, unilamellar vesicles are cleared more slowly from the blood than are MLVs, and exhibit an enhanced distribution to the lungs and possibly bone marrow. Up to the time of the present invention, the methods known for producing these type vesicles relied upon harsh treatment of multilamellar vesicles, such as extrusion through filters, or other physically damaging processes requiring energy input such as sonication, homogenization or milling. Chemical treatment techniques employing harsh detergents or solutions at high or low pH to form unilamellar vesicles have also been employed. The present invention advances the art in that it allows formation of unilamellar vesicles from multilamellar vesicles without the heretofore harsh treatments required, but through the incubation of the liposomes in low ionic strength media at selected temperatures.

Additionally, the unexpected simplicity of preparation of these systems is complemented by the highly defined conditions under which they may be formed. The fact that vesiculation of these lipids occurs only around about the lipid phase transition temperature ($T_c$) and under low ionic strength incubations gives one a high degree of control over vesicle formation. In addition, the characteristic bilayer instability of these systems would be expected to favor interaction of the bilayer with hydrophobic compounds such as drugs, or enhance insertion of membrane proteins or peptides.

SUMMARY OF THE INVENTION

The present invention discloses a method for spontaneously forming unilamellar vesicles from multilamellar vesicles (MLVs). Such MLVs comprise lipids, and unilamellar vesicles are formed by incubating the multilamellar vesicles in low ionic strength medium at neutral pH, around about the transition temperature of the lipids. Preferably the lipids comprise phospholipids, specifically phosphatidylglycerol alone or in combination with phosphatidylcholine, more specifically dimyristoylphosphatidylcholine and dimyristoylphosphatidylglycerol, in a 7:3 mole ratio.

To form the unilamellar vesicles of the invention, the liposomes are incubated at about 22°–26° C., preferably about 24° C. in a medium of between about 0 mM and 25 mM salt. More preferably, the medium comprises about 0–10 mM salt at pH of about 7.0 to about 8.0, preferably pH 7.6 and incubation time is about 15 minutes to about 24 hours.

DETAILED DESCRIPTION OF THE INVENTION

Figure 1:
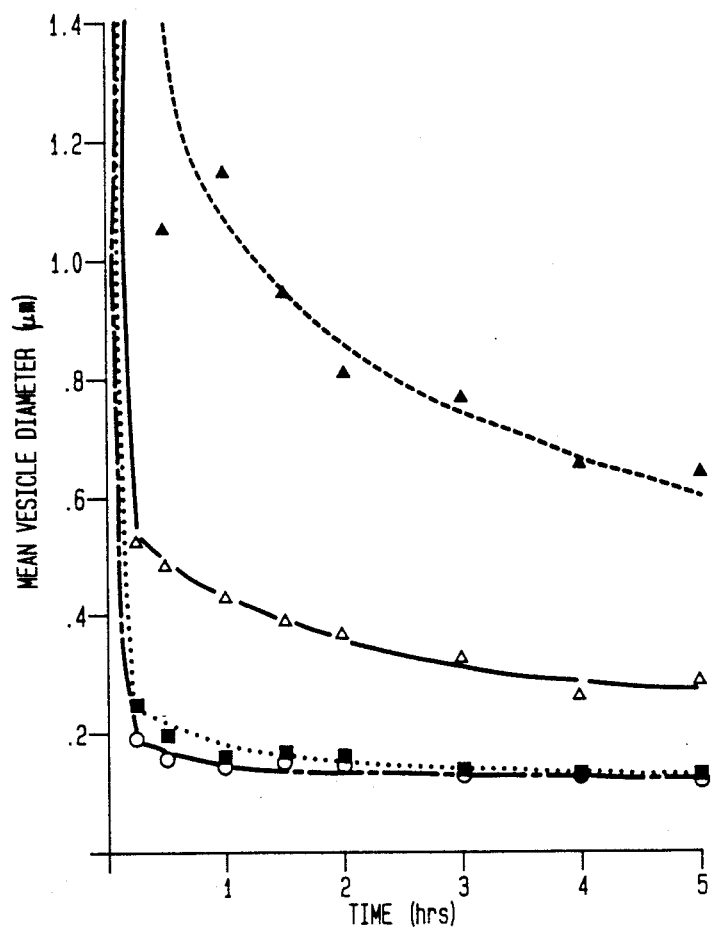
FIG. 1 demonstrates vesiculation of DMPC:DMPG (7:3) MLVs as a function of ionic strength of the incubation medium. DMPC:DMPG (10 mM) was hydrated at 4° C. in the media shown below and incubated at 24° C. (see Examples 1 and 2). Sample media were H$_2$O (open circles); 2 mM HEPES (closed squares); 10 mM NaCl, 2 mM HEPES, pH 7.6, (open triangles); or 25 mM NaCl, 2 mM HEPES, pH 7.6 (closed triangles).

The unilamellar liposomes of this invention are formed by the exposure of multilamellar liposomes to conditions of low ionic strength media at neutral pH, and incubation temperatures around about the gel-to-liquid crystalline transition temperature ($T_c$). Under such incubation conditions, MLVs vesiculate to form unilamellar vesicles. Prior art techniques requiring acidic and alkaline pH variations are not needed in the present method, as vesiculation takes place in a narrow range around neutral pH. The liposomes of the present invention are preferably comprised of phospholipids, specifically dimyristoylphosphatidylglycerol (DMPG) or with dimyristoylphosphatidylcholine (DMPC). Various mole ratios of DMPC and DMPG are suitable for liposome vesiculation, however, the rate of vesiculation decreases with decreasing DMPG concentration.

Upon hydration most naturally occurring phospholipids generally adopt either the bilayer organization or the hexagonal H$_{II}$ phase (Cullis and de Kruijff, 1979, Biochim. Biophys. Acta, 559:339; Cullis et al., 1985, in Phospholipids and Cellular Regulation, J. F. Kuo, Ed., CRC Press, Boca Raton, Florida). In both instances the macromolecular structures formed are large (several microns) and are stable, such that even transitions between these two polymorphic phases do not generate small vesicles. One exception is the case of cardiolipin which in the presence of calcium adopts the hexagonal H$_{II}$ phase. If this mixture is dialyzed against EDTA, small vesicles are generated (Vail et al., 1979, Biochim. Biophys. Acta, 551:74). However, this is presumably due to the removal of calcium from cardiolipin at the exterior of the cylindrical H$_{II}$ arrays and the consequent "blebbing-off" of bilayer vesicles. While large multilamellar vesicles are useful membrane models for investigating the structural and motional properties of lipids, many areas of membrane research and drug delivery require or favor, respectively, the use of unilamellar vesicle systems. Two categories of unilamellar vesicles can be defined. These are small unilamellar vesicles (SUVs) of diameter less than about 50 nm, and large unilamellar vesicles (LUVs) which generally encompass vesicles 50 nm to 1 micron in diameter (Hope et al., 1986, Chem. Phys. Lip., 40:89).

The absence of multiple internal aqueous compartments and the relatively high trapped volumes obtained with LUVs make them useful in a variety of research areas including membrane fusion (Wilschut et al., 1980, Biochemistry, 19:6011) and the in vivo delivery of biologically active compounds (Poznansky et al., 1984, Pharmacol. Rev., 36:227). While MLVs formed by the simple hydration of dry lipid are under osmotic stress due to non-equilibrium solute distribution (Gruner et al., 1985, Biochemistry, 24:2833; Mayer et al., 1986, Biochim. Biophys. Acta, 858:161), they are nevertheless stable structures. The formation of LUVs or SUVs from MLVs usually requires aggressive disruption, for example, by sonication (Huang, 1969, Biochemistry, 8:344) or extrusion through polycarbonate filters (Hope et al., 1985, Biochim. Biophys. Acta, 812, 55), as mentioned above.

While the formation of LUVs from mixtures of phosphatidylcholine with either charged single chain detergents (Hauser et al., 1986, Biochemistry, 25:2126) or short chain phospholipids (Gabriel et al., 1984, Biochemistry, 23:4011) has been described, the only reported instance of MLVs composed solely of bilayer-forming phospholipids spontaneously vesiculating concerns mixtures of acidic phospholipids and phosphatidylcholine transiently exposed to an alkaline pH (Hauser et al., 1982, Proc. Natl. Acad. Sci U.S.A., 79:1683; Hauser, U.S. Pat. No. 4,619,794, issued Oct. 28, 1986, Hauser et al., 1986, Biochemistry, 25:2126; Gains et al., 1983, Biochim. Biophys. Acta, 731:31; Li et al., 1986, Biochemistry, 25:7477).

Since the exposure of membrane lipids to alkaline pH may result in degradation of the lipids and/or any bioactive agent present, and leakage of the vesicle contents, this technique has severe shortcomings in the field of drug delivery employing liposomes. We disclose here that formation of unilamellar vesicles can surprisingly occur at around neutral pH for saturated phosphatidylglycerol and mixtures of saturated phosphatidylcholine and phosphatidylglycerol. Unexpectedly, vesication is rapid only at temperatures around the gel to liquid-crystalline phase transition (the transition temperature or $T_c$, about 22° C. to about 26° C., most preferably about 24° C.), and when hydration or incubation media of low ionic strength are used. When incubation media of high ionic strength (higher than about 50 mM salt) are used, vesiculation occurs at a decreased rate, or not at all. Vesiculation occurs as a function of lowering the ionic strength of the incubation medium. MLVs vesiculate spontaneously when exposed to low ionic strength incubation media (about 10 mM ionic strength and less) when incubated around about the $T_c$ of the lipid. Any ionic species solutions may be used as incubation media, such as the salts sodium chloride, potassium chloride, and others. While a range, therefore, of about 0–25 mM salt in the incubation medium will promote vesiculation, the optimum conditions are around about 0–10 mM salt.

Vesiculation of MLV systems may be determined by incubating the liposomes in low ionic strength medium for 15 minutes to several hours, at around the gel-to-liquid crystalline transition temperature of the lipids used. Whether vesiculation has occurred may be measured by the size of the resulting liposomes using quasi-elastic light scattering, (unilamellar versus multilamellar), visualization of the resulting vesicles using freeze-fracture electron microscopy, and $^{31}P$—NMR analysis of lineshape and spectrum width. For example, narrow spectrum width and isotropic signal is indicative of unilamellar vesicle structure, while a low field shoulder and high field peaks are indicative of larger vesicles.

The lipids of the present invention may be hydrated to form liposomes using any available aqueous solutions, for example, distilled water, saline, or aqueous buffers. Such buffers include but are not limited to buffered salines such as phosphate buffered saline ("PBS"), tris-(hydroxymethyl)-aminomethane hydrochloride ("tris") buffers, and preferably N-2-hydroxyethyl piperazine-N-2-ethane sulfonic acid ("HEPES") buffer. Such buffers are preferably used at pH of about 7.0 to about 8.0, preferably about pH 7.6. If required, the ionic strength of the medium may be adjusted to physiological values following the vesiculation procedure.

The liposomes of the present invention may be dehydrated either prior to or following vesiculation, thereby enabling storage for extended periods of time until use. Standard freeze-drying equipment or equivalent apparatus may be used to lyophilize the liposomes. Liposomes may also be dehydrated simply by placing them under reduced pressure and allowing the suspending solution to evaporate. Alternatively, the liposomes and their surrounding medium may be frozen prior to dehydration. Such dehydration may be performed in the presence of one or more protectants such as protective sugars, according to the process of Janoff et al., PCT 86/01103, published Feb. 27, 1986, and incorporated herein by reference.

The liposomes resulting from the processes of the present invention can be used therapeutically in mammals, including man, in the treatment of infections or conditions which benefit from the employment of liposomes which give for example, sustained release, reduced toxicity, and other qualities which deliver the drug in its bioactive form.

The mode of administration of the preparation may determine the sites and cells in the organism to which the compound will be delivered. The liposomes of the present invention can be administered alone but will generally be administered in admixture with a pharmaceutical carrier selected with regard to the intended route of administration and standard pharmaceutical practice. The preparations may be injected parenterally, for example, intra-arterially or intravenously. The preparations may also be administered via oral, subcutaneous, or intramuscular routes. For parenteral administration, they can be used, for example, in the form of a sterile aqueous solution which may contain other solutes, for example, enough salts or glucose to make the solution isotonic. Other uses, depending upon the particular properties of the preparation, may be envisioned by those skilled in the art.

For the topical mode of administration, the liposomes of the present invention may be incorporated into dosage forms such as gels, oils, emulsions, and the like. Such preparations may be administered by direct application as a cream, paste, ointment, gel, lotion or the like.

For the oral mode of administration, the liposomes of this invention encapsulating a bioactive agent can be used in the form of tablets, capsules, losenges, troches, powders, syrups, elixirs, aqueous solutions and suspensions, and the like. In the case of tablets, carriers which can be used include lactose, sodium citrate and salts of phosphoric acid. Various disintegrants such as starch, and lubricating agents, such as magnesium stearate, sodium lauryl sulfate and talc, are commonly used in tablets. For oral administration in capsule form, useful diluents are lactose and high molecular weight polyethylene glycols. When aqueous suspensions are required for oral use, the active ingredient is combined with emulsifying and suspending agents. If desired, certain sweetening and/or flavoring agents can be added.

The following examples are given for purposes of illustration only and not by way of limitation on the scope of the invention.

EXAMPLE 1

DMPC:DMPG (7:3M ratio) was lyophilized from benzene:methanol (70:30 v/v). The lipid was hydrated to 10 mM with distilled water pH 7.6, at 4° C., forming MLVs. The suspension was then incubated at 24° C. for 15 minutes. QELS studies showed the resulting liposomes to be about 200 nm in diameter, corresponding to LUVs.

The above procedure was followed using 2 mM HEPES buffer as the hydrating solution. QELS measurements revealed LUVs.

This Example demonstrates the formation of unilamellar liposomes by the incubation of a 7:3M ratio of DMPC:DMPG in low ionic strength medium (distilled water, 0 mM salt), at neutral pH. Unilamellar liposomes formed spontaneously when the preparation was incubated at 24° C.

EXAMPLE 2

The procedures and materials of Example 1 were employed using 150 mM NaCl, 2 mM HEPES buffer as the hydrating solution. QELS measurements revealed no change in liposome size (no vesiculation) after incubation.

Figure 2:
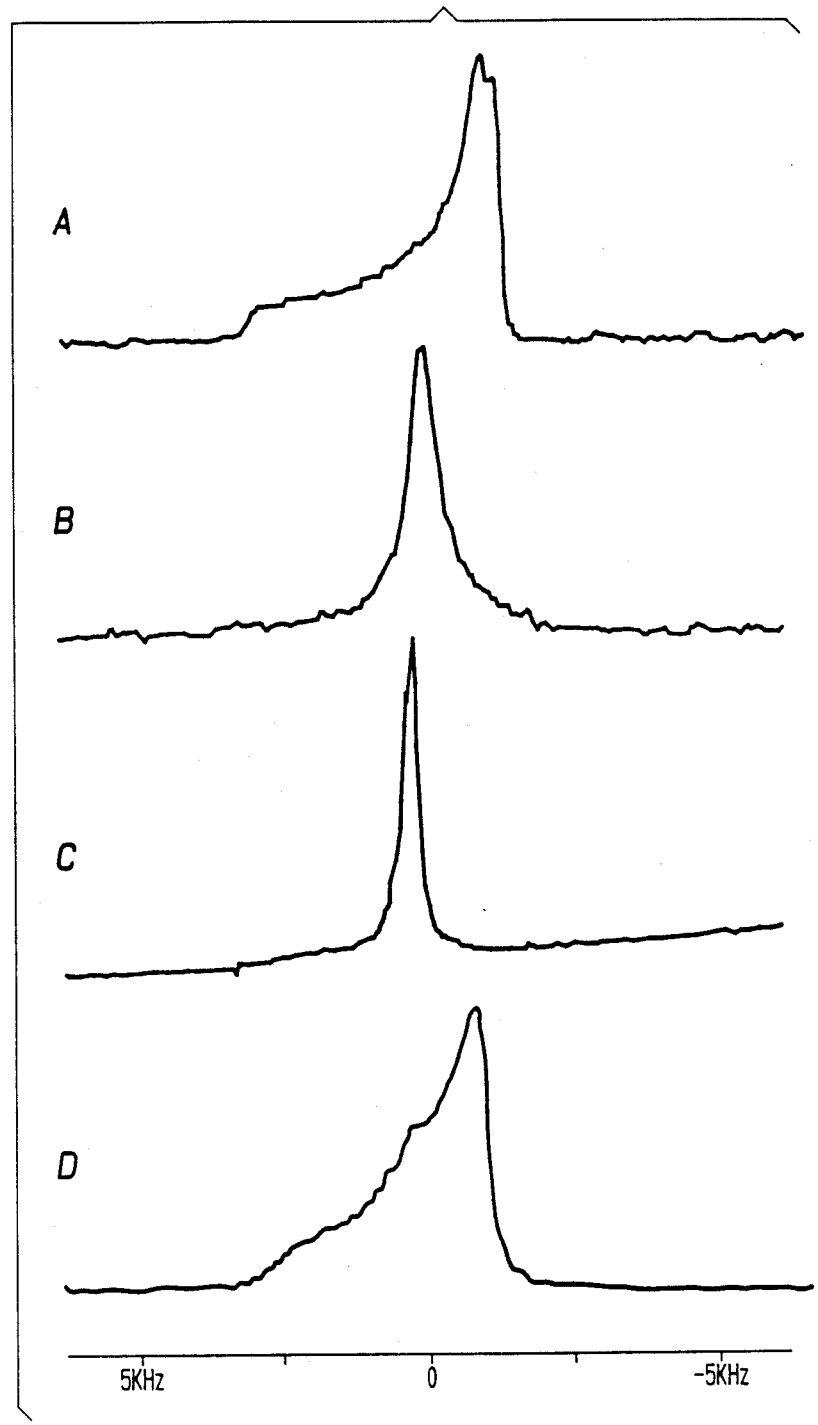
FIG. 2 are $^{31}$P—NMR spectra of DMPC:DMPG. Lipid (10 mM) was hydrated in H$_2$O at 4° C. and its spectrum was recorded at 30° C. (A). The same lipid mixture was then incubated at 24° C. for 1 hour (B) and 12 hours (C). DMPC:DMPG (7:3 mole ratio) hydrated in 150 mM NaCl, 10 mM HEPES, pH 7.6 and incubated at 24° C. for 12 hours is shown in (D).

FIG. 1 demonstrates vesiculation by plotting the vesicle diameter (obtained by quasi elastic light scattering, QELS) as an indication of MLV or LUV against time of incubation, and shows that the rate of vesiculation at 24° C. is directly related to the ionic strength of the hydration medium. FIG. 2 demonstrates the vesiculation by $^{31}$P—NMR spectra of the suspensions; the vesiculated samples (B and C, at low ionic strength incubation) demonstrate the characteristic narrow spectrum and isotropic lipid motion peak which would be expected for vesicles smaller than 400 nm. FIG. 2A and D demonstrate the characteristic bilayer lineshape with low field shoulder and two high field peaks. Plots A and D were recorded from samples incubated under conditions where vesiculation does not occur; at temperatures above the $T_c$, and hydration media of high ionic strength, respectively.

Freeze fracture electron microscopy confirmed the QELS and $^{31}$P—NMR data by allowing visualization of the multilamellar or unilamellar vesicles.

EXAMPLE 3

DMPG (10 mM) was hydrated with 10 mM NaCl, 2 mM HEPES at 4° C., pH 7.6, forming MLVs. These MLVs were incubated at 24° C. for 15 minutes, and the sample analyzed by QELS. The resulting liposomes were unilamellar (LUVs).

This Example may be compared with Example 13, where liposomes made of a 3:7M ratio of DMPC:DMPG incubated in 10 mM NaCl (Example 13) only approach the 200 nm diameter vesicles of Example 3 after 5 hours incubation.

EXAMPLE 4

A 7:3M ratio of dry DMPC:DMPG was equilibrated at 32° C. in a water-saturated atmosphere for 60 minutes, and then the procedures and materials of Example 1 were followed to make MLVs (10 mM lipid), using 2 mM HEPES as hydration medium and an incubation temperature of 32° C. After 6 hours incubation, no vesiculation had occurred as QELS measurements revealed the liposomes had a mean diameter of greater than 2 microns.

The above preparation was then incubated at 24° C. and QELS measurements revealed that the liposomes had vesiculated, resulting in unilamellar vesicles.

This Example is a control for the incubation of the liposome systems around about the $T_c$ of the lipid; it shows this incubation parameter is an important requirement of the invention.

EXAMPLE 5

The procedures and materials of Example 4 were employed using 2 mM HEPES as the hydration medium and an incubation temperature of 15° C. After 6 hours incubation, no vesiculation had occurred as QELS measurements revealed the liposomes had a mean diameter greater than 2 microns.

The above preparation was then incubated at 24° C. and QELS measurements revealed that the liposomes had vesiculated, resulting in unilamellar vesicles.

This Example serves as a further control for $T_c$ being an important incubation parameter. No vesiculation occurred at this incubation temperature. However, when this system was incubated at 24° C., the liposomes rapidly vesiculated.

EXAMPLE 6

A 7:3M ratio of DOPC:DOPG was hydrated with 2 mM HEPES buffer and incubated for 24 hours at 24° C. Samples were analyzed using $^{31}$P—NMR spectroscopy which had a spectrum consistent with bilayer phase lipid organization (FIG. 6K), and the vesicles had a diameter greater than about 400 nm.

EXAMPLE 7

The procedures and materials of Example 1 were employed, using a 7:3M ratio of DOPC:DMPG. The lipid was hydrated with 2 mM HEPES and incubated at 24° C. for 16 hours.

$^{31}$P—NMR spectroscopy revealed little or no vesiculation.

EXAMPLE 8

The procedures and materials of Example 7 were employed, using a 7:3M ratio of DMPC:DOPG. The lipid was hydrated with 2 mM HEPES and incubated at 24° C. for 16 hours.

$^{31}$P—NMR spectroscopy revealed little or no vesiculation.

EXAMPLE 9

The procedures and materials of Example 7 were employed, using a 7:7:3:3M ratio of DOPC:DMPC:DOPG:DMPG. The lipid was hydrated with 2 mM HEPES and incubated at 24° C. for 16 hours.

$^{31}$P—NMR spectroscopy revealed little or no vesiculation.

In this Example, when the gel and liquid-crystalline domains contain both phospholipid species, e.g., DMPC:DOPC:DMPG:DOPG (7:7:3:3), only very limited breakdown of MLV structure is apparent. In these systems the presence of dioleoyl phospholipids stabilizes MLV structure. This Example demonstrates the stability of oleoyl-containing systems. Even when phosphatidylglycerol is present, the dioleoyl species stabilizes mixtures of 7:3M ratio DOPC:DOPG so that incubation at 24° C. in low ionic strength buffer does not induce vesiculation; the systems remain multilamellar.

Figure 3:
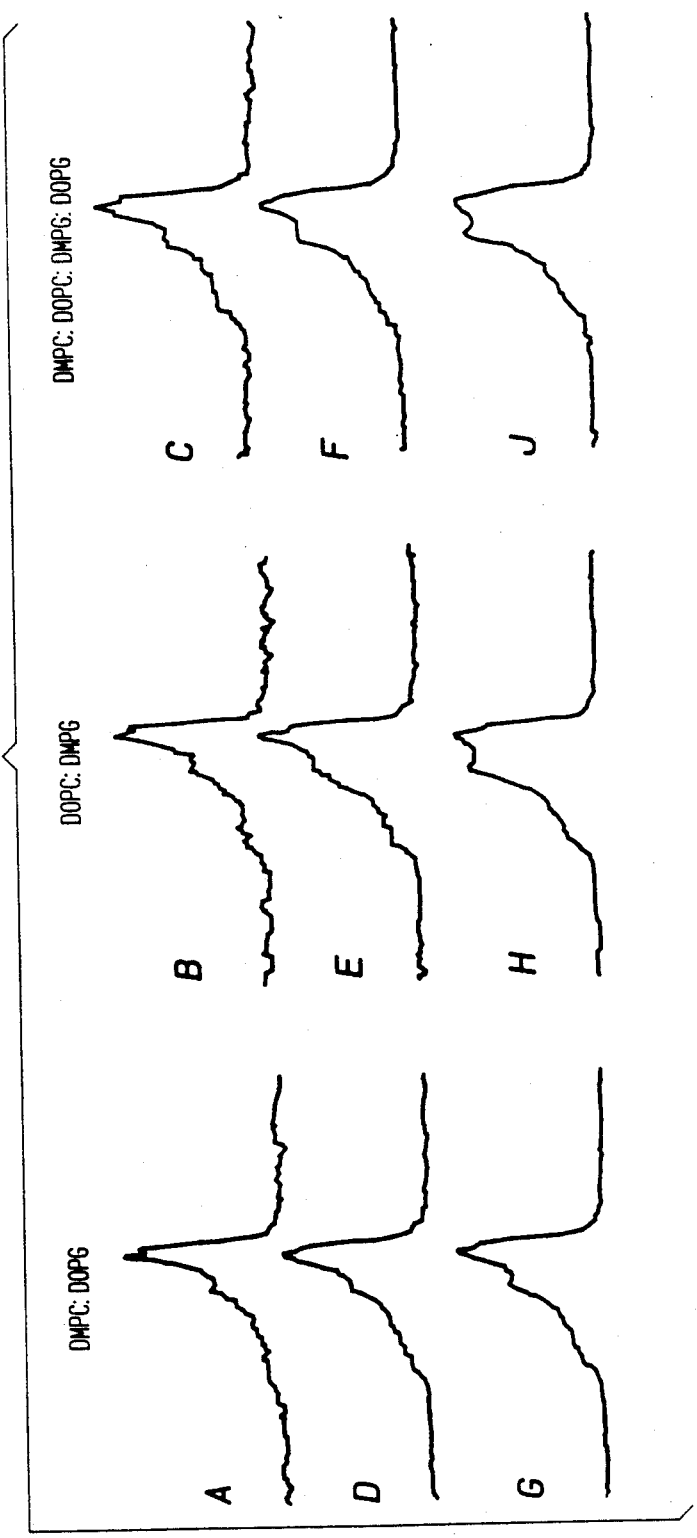
FIG. 3 are $^{31}$P—NMR spectra for mixtures of phosphatidylcholine with phosphatidylglycerol. Lipid (10 mM) was hydrated in 150 mM NaCl, 10 mM HEPES, pH 7.6 (A,B,C,) or 2 mM HEPES, pH 7.6 (D,E,F,G,H,J) and incubated at 24° C. (A,B,C,G,H,J) or 10° C. (D,E,F) for 16 hours.

Further, the stabilizing nature of dioleoyl chains is observed in Examples 7-12 where no vesiculation is observed even when domains of both gel phase lipid (i.e.: dimyristoyl chains) and liquid crystalline phase lipid (i.e.: dioleoyl groups) are present. FIG. 3 (A-J) demonstrates the $^{31}$P—NMR spectra for such samples incubated at either 10° C. or 24° C. All spectra are characteristic of large vesicles in the bilayer phase (MLVs); the samples did not vesiculate.

EXAMPLE 10

The procedures and materials of Example 7 were employed, using a 7:3M ratio of DOPC:DMPG. The lipid was hydrated with 150 mM NaCl, 2 mM HEPES and incubated for 16 hours at 24° C.

$^{31}$P—NMR spectroscopy revealed little or no vesiculation.

EXAMPLE 11

The procedures and materials of Example 7 were employed, using a 7:3M ratio of DMPC:DOPG. The lipid was hydrated with 150 mM NaCl, 2 mM HEPES and incubated for 16 hours at 24° C.

$^{31}$P—NMR spectroscopy revealed little or no vesiculation.

EXAMPLE 12

The procedures and materials of Example 7 were employed, using a 7:7:3:3M ratio of DOPC:DMPC:DOPG:DMPG. The lipid was hydrated with 150 mM NaCl, 2 mM HEPES and incubated for 16 hours at 24° C.

$^{31}$P—NMR spectroscopy revealed little or no vesiculation.

EXAMPLE 13

The procedures and materials of Example 3 were employed, using a 3:7M ratio of DMPC:DMPG. The lipid was hydrated in 10 mM NaCl, 2 mM HEPES at pH 7.6 at 4° C., forming MLVs. The suspension was then incubated for 1 hour at 24° C. QELS measurements revealed that vesiculation of the MLVs had formed LUVs.

What is claimed is:

1. A method for spontaneously forming unilamellar vesicles from multilamellar vesicles comprising incubating a multilamellar lipid consisting essentially of dimyristoylphosphatidylglycerol or its admixtures with dimyristoylphosphatidylcholine in a low ionic strength medium of 50 mM salt or less at neutral pH, at about the gel-to-liquid crystalline transition temperature of the lipid until unilamellar vesicles having a particle size of about 400 nanometers or less are obtained.

2. The method of claim 1 wherein the dimyristoylphosphatidylcholine and dimyristoylphosphatidylglycerol are in a 7:3 mole ratio.

3. The method of claim 2 wherein the liposomes are incubated at about 24° C.

4. The method of claim 1 wherein the liposomes are incubated in medium of between about 0 mM and 25 mM salt.

5. The method of claim 4 wherein the liposomes are incubated in medium of about 10 mM salt for about 15 minutes.

6. The method of claim 1 wherein the liposomes are incubated in medium at pH of about 7.0 to about 8.0.

7. The method of claim 6 wherein the liposomes are incubated in medium at about pH 7.6.

8. The method of claim 1 wherein the multilamellar vesicles consist essentially of dimyristoylphosphatidylglycerol.

9. A method for spontaneously forming unilamellar vesicles from multilamellar vesicles comprising incubating a multilamellar lipid consisting essentially of dimyristoylphosphatidylglycerol or its admixtures with dimyristoylphosphatidylcholine in a medium of about 10 mM salt for about 15 minutes at about 24° C. at pH about 7.6 until unilamellar vesicles having a particle size of about 400 nanometers or less are obtained.

10. The method of claim 9 wherein the multilamellar vesicles consist essentially of dimyristoylphosphatidylglycerol.

* * * * *